United States Patent [19]
Fox et al.

[11] Patent Number: 4,666,892
[45] Date of Patent: May 19, 1987

[54] METHOD AND COMPOSITION FOR HEPATITIS TREATMENT WITH PYRIMIDINE NUCLEOSIDE COMPOUNDS

[75] Inventors: Jack J. Fox, White Plains; Kyoichi A. Watanabe, Portchester; Carlos Lopez, New York, all of N.Y.; Christian G. Trepo, Bron, France

[73] Assignee: Sloan-Kettering Memorial Cancer Center, New York, N.Y.

[21] Appl. No.: 828,569

[22] Filed: Feb. 10, 1986

Related U.S. Application Data

[63] Continuation of Ser. No. 586,729, Mar. 6, 1984, abandoned.

[51] Int. Cl.$^4$ ............................................. A61K 31/70
[52] U.S. Cl. ...................................... 514/49; 514/50; 536/23
[58] Field of Search ................................. 514/49, 50

[56] References Cited

U.S. PATENT DOCUMENTS

| | | | |
|---|---|---|---|
| 4,093,714 | 6/1978 | Tolman et al. | 424/180 |
| 4,210,638 | 7/1980 | Greer | 514/49 |
| 4,211,771 | 7/1980 | Witkowski et al. | 424/180 |
| 4,211,773 | 7/1980 | Lopez et al. | 424/180 |
| 4,382,925 | 5/1983 | de Clerq et al. | 514/49 |
| 4,468,384 | 8/1984 | Bandos et al. | 514/49 |

OTHER PUBLICATIONS

Mochida Pharmaceutical Co., Ltd., 9-(-B-D-Arabinofuranosyl)Adenine Pharmaceuticals for Viral Hepatitis, Chem. Abstracts, 98:78170y (1983).

*Primary Examiner*—Johnnie R. Brown
*Attorney, Agent, or Firm*—John P. White

[57] ABSTRACT

The invention relates to 5-substituted-1-(2'-deoxy-2'-substituted-beta-D-Arabinofuranoysyl) pyrimidine compounds and their use in a method for the treatment of hepatitis B viruses.

9 Claims, No Drawings

METHOD AND COMPOSITION FOR HEPATITIS TREATMENT WITH PYRIMIDINE NUCLEOSIDE COMPOUNDS

This invention was made with Government support under USPHS grants (NCI) CA 18601. The Government has certain rights in this invention.

This application is a continuation of application Ser. No. 586,729, filed Mar. 6, 1984, now abandoned.

BACKGROUND

The hepatitis B virion (HBV), also known as the Dane particle, is a 42 nm complex spherical particle composed of an outer lipoprotein coat (Hepatitis B surface antigen, HBsAg) and an inner core (Hepatitis B core antigen, HBcAG). This core contains a circular partially double stranded DNA and a DNA polymerase. In vitro, the DNA polymerase fills in a large single stranded region in the genome, generating a fully double stranded region in the genome, generating a fully double stranded DNA.

So far, the nature of the Dane particles associated DNA polymerase remains uncertain. Selective inhibition of the HBV DNA polymerase by intercalating agents, pyrophosphate analogs, and arabinofuranosyl nucleotides is known and offers the ability to inhibit hepatitis B virus replication in individuals suffering from chronic hepatitis B. The present invention is concerned with the inhibition of HBV DNA polymerase in vivo by 5-substituted-1-(2'-deoxy-2'-substituted-beta-D-arabinofuranosyl compounds, previously known as antiherpesvirus agents, as reported in U.S. Pat. No. 4,211,773 to Lopez et al.

An agent very closely related to HBV is known in woodchucks: the woodchuck hepatitis virus (WHV). Both agents belong to the same new class of viruses, sometime designated Hepa-DNA viruses. As previously suggested, HBV and WHV DNA polymerases do share the same basic features. The WHV DNA polymerase activity was therefore studied in parallel with that of HBV in the initial in vitro work described below.

BRIEF DESCRIPTION

The invention is a method and composition for treatment of in vitro hepatitis virus infection. More specifically the invention provides a method and composition for treatment of woodchuck hepatitis virus infection in woodchucks and hepatitis B virion infection in man using anti-virally active 5-substituted 1-(2'-deoxy-2'-substituted-beta-D-arabinofuranosyl) pyrimidine nucleosides as described and claimed in U.S. Pat. No. 4,211,773.

DETAILED DESCRIPTION

Preparation of Virus Particles

HBV particles containing DNA polymerase activity were purified from the serum of an immunosuppressed patient, positive for HBsAg. WHV was obtained from a serum pool of five woodchucks (*Marmota monax*) chronic carriers of the virus. The woodchucks initially imported from Pennsylvania (Dutchland Lab. Pennsylvania, USA) belonged to a colony followed for over one year by serological tests (Hantz et al, J. Virol. Metho. 7, 45–55 (1983)).

Virus was purified by centrifugation on sucrose and isopycnic CsCl gradients. (Hantz et al submitted for publication).

Chemicals

For in vitro testing, triphosphates were used. This is required because of expected cell metabolism processes.

Unlabelled nucleoside triphosphates were obtained from Sigma (Chemical Company, St. Louis, USA). Tritiated deoxyribonucleoside triphosphates, [$^3$H] dTTP (30 Ci/mmol), $^3$H] daTP (24 Ci/mmol), [$^3$H] dCTP (17 Ci/mmol) and [$^3$H] dCTP (9,5 Ci/mmol), were obtained from Amersham (Amershal France). ACV was obtained from Burroughs Wellcome, Chapel Hill NC; the synthesis of BVdU is described by DR CLERCO et al (Proc. Natl. Acad. Sci. U.S.A., 76, 2947-2951 (1979)) FIAC synthesis is described in Lopez et al (U.S. Pat No. 4,211,773). All the three nucleoside analogs were converted to their corresponding 5'-triphosphates by procedure described by Allaudeen et al (Proc. Natl. Acad. Sci. U.S.A. 78, 2698-2702 (1981)). The purity of the triphosphates was examined by 'H NMR on a Bruker HX-270 spectrometer and by high pressure liquid chromatography on an Altex Model 332 gradient liquid chromatograph.

DNA polymerase assay:

DNA polymerase was assayed as described by Kaplan et al (J. Virol., 12, 995 (1973)) with minor modification. The assay was performed in a 50 ul reaction mixture containing 50 mM Tris-HCl pH=7,6,40 mM MgCl2, 60 mM NH4 Cl, 100 uM each dATP, dCTP and dGTP, 0.2-0.7 uM [$^3$H] dTTP (30 Ci/mmol), 10 mM 2-mercaptoethanol, 0.5% Nonidet P 40 and enzyme. The reaction was started by addition of the virus particles with 2-mercaptoethanol and Nonidet P 40. Incubation was at 37° C. for 1 h. Acid insoluble radioactive material was collected on a glass fiber filter (GF/C Whatman) Filters were washed 5 times with cold 5% trichloracetic acid containing 10 mM sodium pyrophosphate, then with 95% ethanol. Radioactivity of the dried filter was measured in a liquid scintillation counter.

Agarose gel electrophoresis of [$^{32}$p] DNA

The [$^{32}$p] DNA product by the endogenous DNA polymerase reaction was analysed by agarose gel electrophoresis as described by Summers et al (Proc. Natl. Acad. Sci. U.S.A. 72, 4597-4601 (1975)). The reaction was made in 15 ul of the standard DNA polymerase mixture with 1 uM of [$^{32}$p] dCTP (500 Ci/mmol) as labelled nucleotide.

After 2 h incubation at 37° C., the reaction was terminated by the addition of 20 ul of 10 mM Tris, 10 mM EDTA, 0, 1 mg per ml of proteinase K, 0, 1% (wt/vol) sodium dodecyl sulfate, followed by further incubation for 60 mn at 37° C. 5 ul of 5% (wt/vol) sucrose, 1% bromophenol blue was added, the entire mixture was heated for mn at 65° C., immediately colded at 4° C. and then analyzed by electrophoresis on a horizontal slab gel of 1% agarose. After electrophoresis, the gel was dried and developed by autoradiography.

DISCUSSION

Product of HBV and WHV DNA polymerase reaction

The specificity and the efficiency of the DNA polymerase in the HBV and WHV particle preparations were controlled by analysis of the labelled DNA synthesized during the endogenous reaction. The DNA polymerase assay was made as described in the methods with [$^{32}$P] labeled nucleotide. The product of the reaction was then analyzed by agarose gel electrophoresis and autoradiography. The results show the progressive synthesis of HBV and WHV DNA after 15, 30, 120 and 180 mn of reaction. For HBV, a complete 3.3 kb long DNA and smaller forms (from 1.8 to 28 kb) corresponding to an incomplete filling of the single stranded region of the viral genome were obtained. The product of the WHV DNA polymerase reaction was more heterogeneous and migrated slightly faster; after 180 mn of the reaction the longer form of WHV DNA was 3.1 kb long.

Relative sensitivities of HBV and WHV, DNA polymerase to ACVTP FIACTP AND BVdUTP The relative sensitivities of both enzymes to CVTP, FIACTP and BVdUTP were compared using an excess of nucleotides. For each inhibitor, the concentration of the corresponding radioactive triphosphate was maintained at 2 to 3 times the Km value while the remaining nucleotides were in great excess (50 uM). Results show that FIACTP was the most efficient inhibitor of HBV DNA polymerase and ara-CTP was the least efficient; BVdUTP and ara-TTP showed a similar inhibition.

We obtained similar results with WHV DNA polymerase. The concentrations of triphosphates required to inhibit 50 percent of HBV and WHV DNA polymerases were determined and showed that $ID_{50}$ of FIACTP was very low (0,05 uM) compared with the values obtained for BVdUTP and ACVTP which were 5 and 18 times more, respectively.

Kinetics of inhibition

Although the mode of action for the various compounds is known to be different, the nature of ACVTP, FIACTP and BVdUTP inhibition of viral DNA synthesis catalyzed by HBV and WHV DNA polymerases was examined by determining the extent of inhibition with increasing concentrations of the substrates. In assays with ACVTP, [$^3$H] dGTP was the rate limiting substrate while the other three nucleotides were in excess. The same conditions were used with [$^3$H] dCTP for FIACTP and [$^3$H] dTTP for BVdUTP inhibition. Lineweaver-Burk plots show that the inhibition of HBV DNA polymerase reaction by ACVTP, FIACTP and BVdUTP was competitive with dGTP, dCTP and dTTP, respectively. Similar results were obtained for WHV DNA polymerase. The Km value of dGTP, dCTP, dTTP and the Ki value of ACVTP and BVdUTP for the DNA polymerases of both viruses was determined WHV DNA polymerase showed a lower affinity to ACVTP, FIACTP and BVdUTP than HBV DNA polymerase; however, the Km.Ki ratios were comparable for both enzymes.

Effect of BVdUTP, FIACTP and ACVTP on DNA synthesis in vitro

To determine the effect of the three analogs on viral DNA synthesis, a time course experiment was performed with HBV DNA polymerase. [$^3$] dATP was used as the labelled substrate. With all four nucleoside triphosphate substrates, the reaction was linear up to 60 mn When dTTP, dCTP of dGTP was ommitted from the reaction mixture, no significant DNA synthesis was observed. The substitution of dTTP by BVdUTP permitted the viral DNA syntheses up to 46 percent of the control after 3 h of reaction. This value increased to 67 percent of the optimal activity after 4 h of reaction. However, in a similar experiment, no significant DNA synthesis was observed when dTTP was substituted by ara-TTP. When such an experiment was performed with FIACTP instead of dCTP a low incorporation of [$^3$H] d AMP was obtained (about 10% of the control after 3 h of reaction) while no significant incorporation was observed when ara-CTP was used instread of dCTP. The substitution of dGTP by ACVTP did not increase the polymerization process. The efficiency of these different analogs to the alternate substrates of HBV and WHV DNA polymerases show that BVdUTP was the most efficient alternate substrate for both enzymes. The DNA synthesized with BVdUTP as alternate substrate was analyzed by agarose gel electrophoresis. Only incomplete filling of the single stranded region of HBV or WHV DNA was obtained with BVdUTP.

The effect of ACVTP on HBV DNA synthesis was also studied in a time course experiment $^3$H] dTTP was the labelled substrate. The reaction was initiated without dGTP or with 5 um ACVTP instead of dGTP. Under these conditions, no incorporation of [$^3$H] dTMP could be measured. After 120 min of reaction, 100 uM of dGTP was added. In the assay without dGTP only, the addition of dGTP increased DNA synthesis as expected. However, when the assay was first made with 5 uM ACVTP instead of dGTP, no DNA synthesis was observed after addition of 100 um dGTP. By comparison, when the reaction was started with the same proportion of ACVTP (5 uM) and dGTP (100 uM0 a significant DNA synthesis was observed. Similar experiments were carried out with ara-ATP and ara-CTP. In both cases the addition of normal substrate (dATP and dCTP) after 120 mn of reaction in presence of the analog increased the HBV DNA synthesis. Thus, addition of ACVTP instead of the natural triphosphate substrate, dGTP did not enhance DNA synthesis but seemed to block further elongation.

DISCUSSION

Nucleoside analogs demonstrating antiviral activity have to be converted to their triphosphate derivatives within the cell to interfere with viral DNA synthesis. Preferential inhibition of herpes simplex virus DNA polymerase by CVTP, BVdUTP and FIACTP have been reported and may explain in part the selective antiviral activity of nucleoside analogs ACV, BVdUTP and FIAC. The in vitro evidence described above, shows that all the three compounds inhibit the DNA polymerases of HBV and WHV and that the inhibition is competitive with the corresponding natural triphosphate substrates. The respective inhibitory activities of ACVTP, BVdUTP, FIACTP and two other nucleotide analogs, ara-CTP and ara-TTP were compared. Inhibitory activity on HBV and WHV DNA polymerases decreased in the following order: FIACTP, BVdUTP, ara-TTP, ACVTP, ara-CTP.

In vivo inhibition of HBV replication by ACV has been demonstrated in patients with chronic hepatitis B (Weller et al, Lancet, 1, 273 (1982); Weller et al, J. Antimicrob. Chemother. 11, 223-231 (1983)); whether the in vivo effect of ACV can be related to the in vitro inhibitory action of ACVTP on HBV DNA polymerase remains uncertain since the role of the endogenous DNA polymerase in HBV replication within the infected cells remains unknown. Moreover, an important step in the action of anti-herpesviral agents such as ACV, FIAC and BVdU is the selective phosphorylation of these analogs in the infected cells by the herpesvirus encoded thymidine kinase. So far, no viral thymidine kinase activity has been reported for HBV or WHV. Thus, this in vitro work cannot be directly related to possible in vivo use of these materials. Also, because the mode of operation for each compound is different, it cannot be predicted that the in vivo activity of one is related to the in vivo activity of the other.

However, in the absence of any cell culture system for the growth of HBV, inhibition study of the HBV endogenous DNA polymerase reaction remains the only useful screening test to identify potential anti HBV agents.

Based on this data, FIAC and related anti-herpes virial effective pyrimidine nucleoside compounds (5-substituted-1-(2'-deoxy-2'-substituted-beta-D-arabinofuranosyl) pyrimidine nucleoside compounds) will be used to treat hepatitis B virus infection in man and woodchuck hepatitis virus infection in woodchucks. FIAC and related compounds were selected because of their superior activity as compared with the other agents tested in vitro. It is anticipated that the activity of these compounds will be vastly superior to the activity of the other classes of compounds against which they were treated in vitro, as reported above.

In Vivo Testing

Testing will be done on humans and on woodchucks. The compounds to be tested will include the pyrimidine nucleoside compounds: FIAC (2'-fluoro-2'-deoxy-arabinosyl-5-iodocytosine), FIAU (2'-fluoro-2'-deoxy-arabinosyl-5-iodouracil) and, FMAU (2'-fluoro-2'-deoxy-arabinosyl-5-methyluracil or 2'-fluoro-2'-deoxy-arabinosyl-5-thymine).

These compounds are soluble in water and therefore water or water based solutions are preferred as solvents for treating patients. The solubilities are as follows:

|      |           |        | Mol. Wt. |
|------|-----------|--------|----------|
| FIAC | 7.2 mg/ml | at 21° | 371      |
| FMAU | 66 mg/ml  | at 24° | 260      |
|      | 81 mg/ml  | at 28° |          |
| FIAU | 4 mg/ml   | at 28° | 372      |

The solubility of these compounds can be increased by adding acid or base to the aqueous solvent. In this way, FIAC solubility can be increased to about 250 mg/ml by adding about one molar equivalent of hydrochloric acid, although somewhat less concentrated hydrochloric acid will work. For FIAU, the solubility can be increased many fold by adding one equivalent of sodium hydroxide—which makes the sodium salt of FIAU.

Dosages for treating humans will be as follows:

FIAC up to 400 mg/m² per day and preferably 120 mg/m² per day, for up to 7 days for each treatment, as required. Dosages of about one-half the preferred rate are minimum amounts that can practically be used. Below this amount, the effects of the drugs is too small. Thus, for FIAC about 60 mg/m² is a minimum practical dosage.

FIAU is to be used at the same dosage ranges as FIAC. It is noted that FIAU is a metabolite of FIAC and is expected to be useful in the same dosage ranges.

FMAU up to 32 mg/m² per day preferably 16 mg/m² (to avoid some side effects) and most preferably about 4 mg/m² per day for up to 7 days for each treatment, as required. About one-half the most preferable dosage or about 2 mg/m² is the minimum practical dosage amount.

Dosages above the maximum amounts stated can result in undesirable side effects.

Similar treatments will be accomplished on woodchucks to inhibit the replication of hepatitis B Type virus as follows. The dosages to be used are in the same range as that used in humans, measured in mg/m² per day.

It will be understood that the specification and examples are illustrative but not limitative of the present invention and that other embodiments within the spirit and scope of the invention will suggest themselves to those skilled in the art.

What is claimed is:

1. A method for the treatment of hepatitis B virus infection in an infected human comprising
administering an effective amount to inhibit hepatitis B virion replication, 5-substituted-1-(2'-deoxy-2'-substituted-beta-D-arabinofuranosyl)pyrimidine compound of the formula

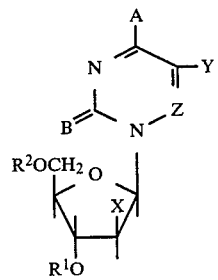

wherein

A is OR³, SR³, NR³R⁴ or NHacyl wherein R³ and R⁴ are the same or different and are hydrogen, lower alkyl of 1 to 7 carbon atoms, aralkyl, or aryl;

NHacyl is alkanoyl or aroyl amide;

B is oxygen or sulfur;

X is halogen

Y is halogen, amino, monoalkyl- or monoaralkylamino, dialkylamino, aminomethyl, hydroxymethyl, lower alkyl, aryl, aralkyl, vinyl and substituted vinyl or ethynyl and substituted ethynyl;

Z is methyne or nitrogen;

R¹ and R² are the same or different and are hydrogen acyl or aroyl.

2. The method of claim 1 wherein the pyrimidine compound is administered intravenously.

3. The method of claim 1 wherein the pyrimidine compound is administered orally.

4. A method of treating hepatitis B virus infection comprising administering an effective amount of FIAC.

5. The method of claim 4 wherein up to 400 mg/m² of FIAC are used per day.

6. A method of treating hepatitis B virus infection comprising admininstering an effective amount of FMAU.

7. The method of claim 6 wherein up to 32 mg/m² of FMAU are used per day.

8. A method of treating hepatitis B virus infection comprising administering an effective amount of FIAU.

9. The method of claim 1 wherein up to 400 mg/m² of FIAU are used per day.

* * * * *